US00PP10594P

United States Patent [19]

Bergman

[11] Patent Number: Plant 10,594

[45] Date of Patent: Sep. 8, 1998

[54] HIBISCUS PLANT NAMED 'KONA WIND'

[75] Inventor: Wendy R. Bergman, Lehigh Acres, Fla.

[73] Assignee: Yoder Brothers, Inc., Barberton, Ohio

[21] Appl. No.: 807,405

[22] Filed: Feb. 27, 1997

[51] Int. Cl.[6] ..... A01H 5/00

[52] U.S. Cl. ..... Plt./67.8

[58] Field of Search ..... Plt./67.8

*Primary Examiner*—James R. Feyrer

*Attorney, Agent, or Firm*—C. A. Whealy

[57] ABSTRACT

A new and distinct cultivar of Hibiscus plant named 'Kona Wind', characterized by its very dark green leaves; upright and outwardly spreading, uniform and symmetrical plant habit; early flowering; freely flowering, numerous bright orange and golden yellow-colored flowers with dark red throats; good resistance to flower bud abscission; and excellent postproduction longevity.

3 Drawing Sheets

The present invention relates to a new and distinct cultivar of Hibiscus, botanically known as *Hibiscus rosa-sinensis,* and hereinafter referred to by the cultivar name Kona Wind.

The new cultivar is a product of a planned breeding program conducted by the inventor in Alva, Fla. The objective of the breeding program is to create new Hibiscus cultivars having uniform plant habit, early flowering, numerous flowers per lateral branch, desirable flower color, resistance to flower bud abscission, and good postproduction longevity.

The new cultivar originated from a cross made by the inventor in Alva, Fla. of the proprietary seedling selection identified as number 0602 as the female, or seed, parent with the commercial cultivar Waikiki (disclosed in U.S. Plant Pat. No. 7,834) as the male, or pollen, parent. Compared to plants of the proprietary seedling selection number 0602, plants of the new Hibiscus are more compact, have glossier leaves and flower earlier. Compared to plants of the pink-colored cultivar Waikiki, plants of the new Hibiscus have undulating leaves whereas leaves of plants of the cultivar Waikiki are not undulating.

The cultivar Kona Wind was discovered and selected by the inventor as a flowering plant within the progeny of the stated cross in a controlled environment in Alva, Fla., on Aug. 24, 1993. The selection of this plant was based on its desirable flower color, resistance to flower bud abscission, good postproduction longevity, and uniform plant habit and flowering.

The new Hibiscus is similar to plants of the nonpatented cultivar Euterpe. However, in side-by-side comparisons conducted in Alva, Fla. plants of the new cultivar differ from plants of the cultivar Sundance in the following characteristics:

1. Plants of the new Hibiscus are more compact than plants of the cultivar Euterpe.
2. Plants of the new Hibiscus flower more uniformly than plants of the cultivar Euterpe.
3. Plants of the new Hibiscus have a darker, more intense flower color than plants of the cultivar Euterpe.
4. Plants of the new Hibiscus are more resistant to flower bud abscission than plants of the cultivar Euterpe.
5. Plants of the new Hibiscus flower about 10 days earlier than plants of the cultivar Euterpe.

Asexual reproduction of the new cultivar by terminal cuttings taken in a controlled environment in Alva, Fla., has shown that the unique features of this new Hibiscus are stable and reproduced true to type in successive generations.

The cultivar Kona Wind has not been observed under all possible environmental conditions. The phenotype may vary somewhat with variations in environment such as temperature, light intensity, nutrition and water status without, however, any variance in genotype.

The following traits have been repeatedly observed and are determined to be the unique characteristics of 'Kona Wind'. These characteristics in combination distinguish 'Kona Wind' as a new and distinct cultivar:

1. Very dark green leaves.
2. Upright and outwardly spreading, uniform and symmetrical plant habit.
3. Early flowering.
4. Freely flowering, numerous bright orange and golden yellow-colored flowers with dark red throats.
5. Good resistance to flower bud abscission.
6. Excellent postproduction longevity.

The accompanying colored photographs illustrate the overall appearance of the new cultivar, showing the colors as true as it is reasonably possible to obtain in colored reproductions of this type.

The first photograph comprises a side perspective view of typical plant of 'Kona Wind'.

The second photograph comprises a close-up view of a typical flower of 'Kona Wind'.

The third photograph comprises a close-up view of typical flowers of the cultivar Euterpe, left, and the cultivar Kona Wind, right. Flower and foliage colors in the photographs may appear different from the actual colors due to light reflectance.

The aforementioned and following observations, measurements, values, and comparisons describe plants grown in Alva, Fla., in 15-cm containers with day temperatures ranging from 16 ° to 35° C. and night temperatures ranging from 10 ° to 24° C. Plants were grown under a polypropylene covering with light levels ranging from 6,000 to 9,000 footcandles.

In the following description, color references are made to The Royal Horticultural Society Colour Chart except where general terms of ordinary dictionary significance are used.

Botanical classification: *Hibiscus rosa-sinensis* cv. Kona Wind.

Parentage:

*Male or pollen parent.*—*Hibiscus rosa-sinensis* cv. Waikiki (U.S. Plant Pat. No. 7,834).

*Female or seed parent.*—Proprietary seedling selection of *Hibiscus rosa-sinensis* identified as number 0602.

Propagation:

*Type.*—By terminal cuttings.

*Time to develop roots.*—About 28 days at temperatures of 24° C.

*Rooting habit.*—Moderately vigorous, thick and well-branched.

Plant description:

*Plant form and growth habit.*—Perennial, evergreen, upright and outwardly spreading, inverted triangle, uniform and symmetrical plant habit. Moderate vigor.

*Branching habit.*—Moderate, usually three lateral branches develop after removal of terminal apex.

*Plant height, soil level to top of flowers.*—About 26 cm.

*Plant diameter, area of spread.*—About 40 cm.

*Lateral branch description.*—Length: About 8 cm. Diameter: About 5 mm. Color: Immature: 146A. Mature: Green, 147A, with 197B overtones.

Foliage description:

*Arrangement.*—Alternate, single.

*Leaf size, largest leaves.*—Length: About 7.5 cm. Width: About 7.5 cm.

*Leaf shape.*—Ovate.

*Leaf apex.*—Acute.

*Leaf base.*—Cordate.

*Margin type.*—Dentate.

*Texture.*—Glabrous and glossy on both surfaces.

*Aspect.*—Undulating.

*Color*: Young foliage, upper surface: Greener than 146A. Young foliage, lower surface: 146A. Mature foliage, upper surface: Very dark green, darker than 147A. Mature foliage, lower surface: 147A. Venation, upper surface: 147A. Venation, lower surface: 146A.

*Petiole.*—Length: About 2.5 cm. Diameter: About 4 mm. Texture: Glabrous. Color: 146A.

Flower description:

*Natural flowering season.*—Usually spring and summer or during periods of warm weather.

*Flower arrangement.*—Flowers arranged singly at terminal leaf axils. Very freely flowering with usually five to six flower buds and/or open flowers per terminal apex. Flowers face upright or outward.

*Flower appearance.*—Star-shaped single. Bright orange and golden yellow-colored petals with dark red throat. Flowers are open for about one day before closing. Flowers persistent.

*Flower diameter.*—About 14 cm.

*Flower bud* (*just before opening*).—Rate of opening: About one day depending on temperatures. Length: About 7 cm. Diameter: About 1.5 cm. Shape: Columnar. Color: Bright orange red, close to 40B.

*Petals.*—Texture: Satiny, smooth. Arrangement: Corolla consists of five petals that overlap. Shape: Spatulate with rounded apex. Margin: Entire. Size: Length: About 8 cm. Width: About 6.5 cm. Color: Upper surface: Bright orange, 28B/25A, at margins with golden yellow, 22B at centers. Veins are dark red, 53B. Upper surface: Golden yellow, 22B, with orange where petals overlap and light pink to white at base. Throat: Dark red, 53A/53B. After closing: Apex: 25A. Mid-section: 22D. Base: Light pink to white.

*Sepals.*—Appearance: Six sepals fused into a star-shaped calyx. Shape: Linear. Texture: Smooth. Color, upper surface: 146A.

*Peduncles*—Length: About 6 cm. Diameter: About 3 mm. Angle: Upright. Strength: Strong, rigid. Color: 146A.

*Reproductive organs.*—Androecium: Stamen number: Numerous. Stamen length: About 5 mm. Anther shape: Globular. Anther size: About 1 mm. Amount of pollen: Abundant. Pollen color: 21A. Gynoecium: Pistil length: About 10 cm. Style length: About 7.5 cm. Style color: 39C. Stigma shape: Round. Stigma diameter: About 2.5 mm. Stigma color: 45B. Ovary color: White.

Disease resistance: No known Hibiscus diseases observed to date on plants grown under commercial greenhouse conditions.

Seed production: If cross-pollinated, seed production may be observed. Usually one to twenty seeds per capsule.

It is claimed:

1. A new and distinct Hibiscus plant named 'Kona Wind', as illustrated and described.

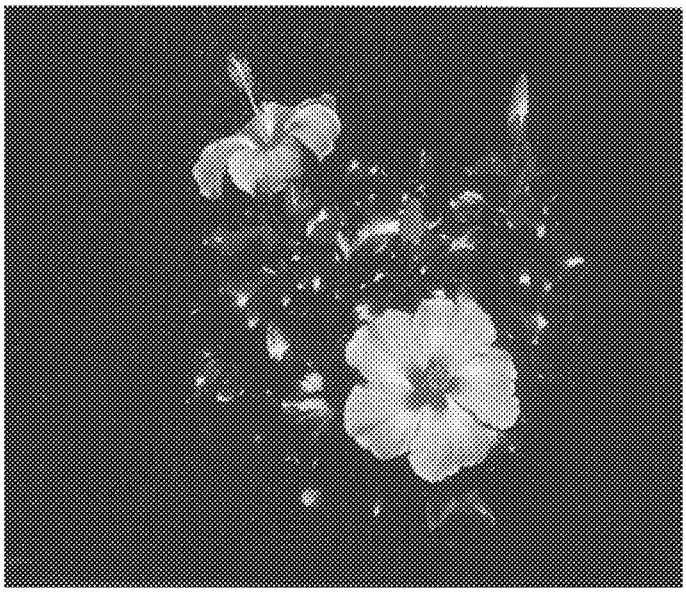

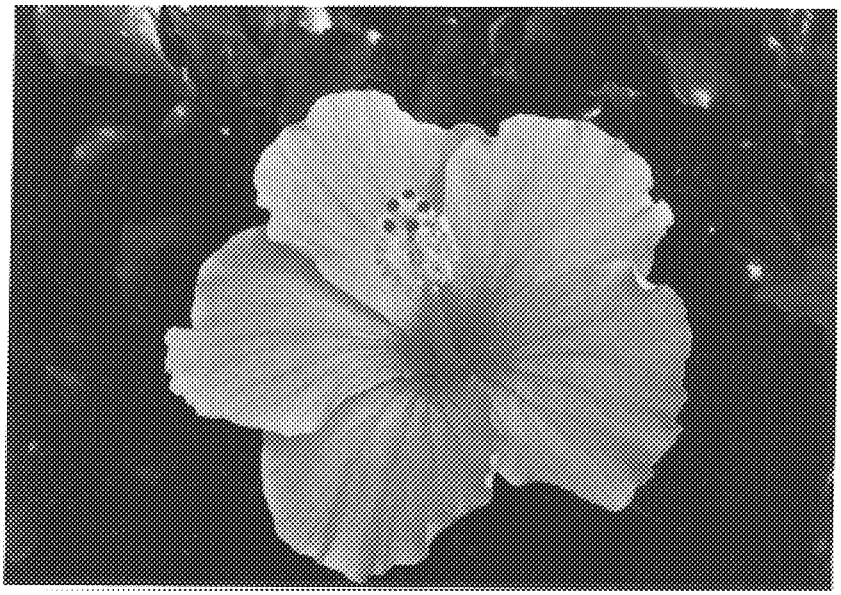

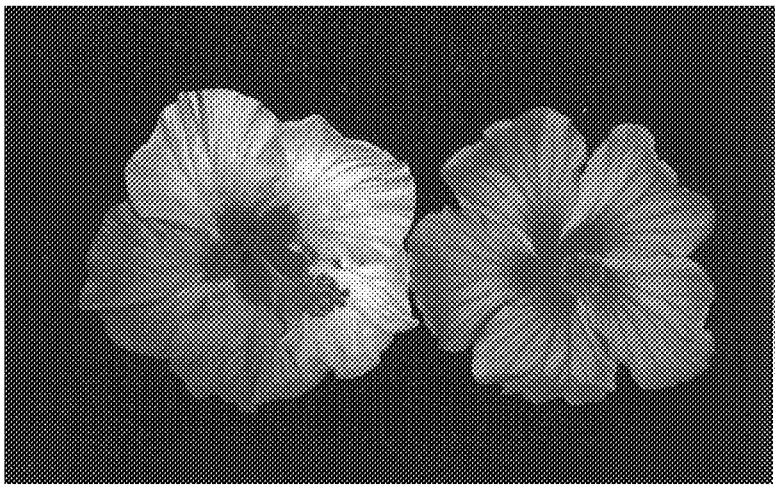

* * * * *